United States Patent [19]
Lekholm

[11] Patent Number: 5,623,957
[45] Date of Patent: Apr. 29, 1997

[54] VALVE FOR CONTROLLING A GAS OR LIQUID FLOW

[75] Inventor: Anders Lekholm, Bromma, Sweden

[73] Assignee: Siemens-Elema AB, Solna, Sweden

[21] Appl. No.: 379,951

[22] Filed: Jan. 27, 1995

[30] Foreign Application Priority Data

Feb. 4, 1994 [SE] Sweden ................... 9400366

[51] Int. Cl.⁶ ..................... F16K 13/10; F16K 31/08
[52] U.S. Cl. ............................. 137/246; 251/65
[58] Field of Search ...................... 137/246; 251/65

[56] References Cited

U.S. PATENT DOCUMENTS

| | | | |
|---|---|---|---|
| 1,533,793 | 4/1925 | Failla | 137/246 |
| 3,799,427 | 3/1974 | Goglio | 137/246 X |
| 4,444,219 | 4/1984 | Hollenstein | 137/246 |
| 4,883,467 | 11/1989 | Franetzki et al. | 604/152 |
| 4,890,637 | 1/1990 | Lamparter | 137/246 |
| 5,354,133 | 10/1994 | Rapparini | 137/246 X |

FOREIGN PATENT DOCUMENTS 0117149  8/1984  European Pat. Off. .

OTHER PUBLICATIONS

Abstract For Soviet Union, Registration SU 872883, Oct. 1981.

*Primary Examiner*—John Rivell
*Attorney, Agent, or Firm*—Hill, Steadman & Simpson

[57] ABSTRACT

A valve for controlling a gas or liquid flow, has an admission and a discharge with a valve seat, a valve part displaceable relative to the valve seat, and a seal therebetween, whereby the valve part presses the seal against the valve seat in one position and thus interrupts the flow. In order to obtain a valve of this type that has a simple structure and exhibits an extremely high sealing power over a comparatively long time span, a liquid having such properties that it is insoluble in the liquid or the gas that flows through the valve serves at least partially as a seal.

13 Claims, 4 Drawing Sheets

FIG 5
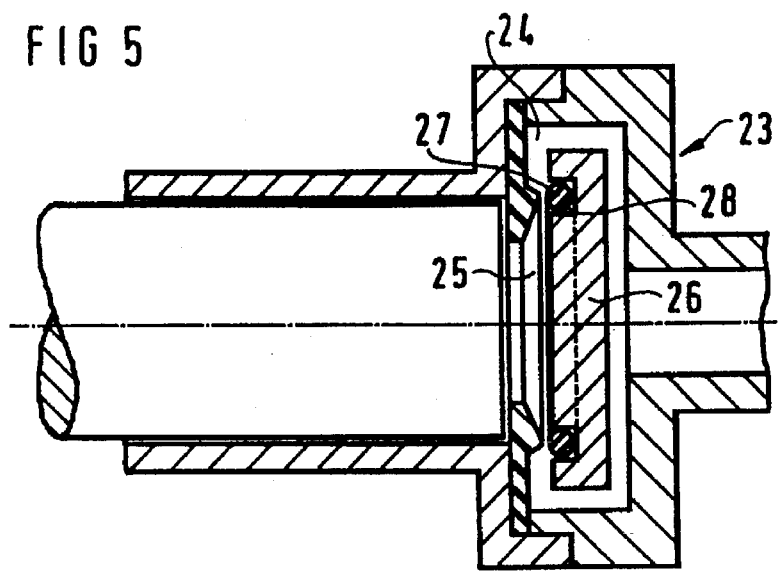
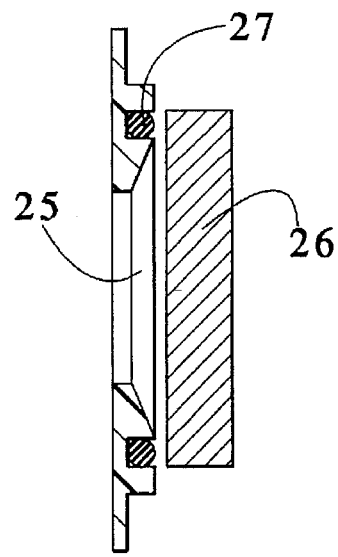
FIG. 5a
FIG 6
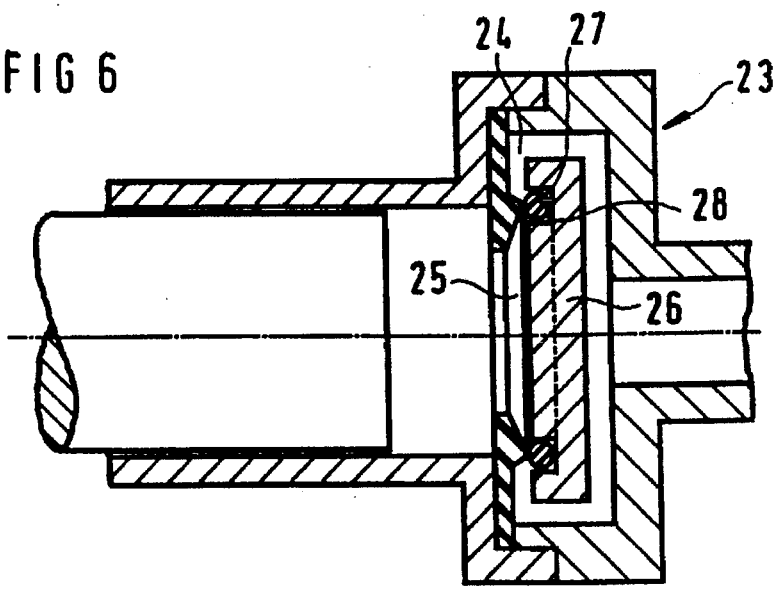

VALVE FOR CONTROLLING A GAS OR LIQUID FLOW

BACKGROUND OF THE INVENTION

1. Field of the Invention

The present invention is directed to a valve for controlling a fluid (gas or liquid) flow, of the type having an admission and a discharge with a valve seat, a valve part displaceable relative to the valve seat, and a seal therebetween, whereby the valve part presses the seal against the valve seat in one position and thus interrupts the flow.

2. Description of the Prior Art

It is a well-known problem in conventional valves that the valve seat as well as the valve part have imperfections in the region of the surfaces to be sealed, or can be damaged in such a way that leakage can occur. After some time, an elastic seal or packing can also harden or deform, so that a valve that was initially functional becomes unusable over time. In the case of an apparatus wherein high precision in the dosing of a fluid is required, particularly when the valve should also allow extremely slight quantities to pass, it is of great importance that this valve seal well even after a longer service time.

One device whose valves must have an extremely high sealing power is an implantable medication dosing pump for insulin dosing, whereby the medication is to be administered in extremely small doses having a volume of approximately 1 μl. Such a device that is provided with a conventional valve of the type initially described is disclosed in U.S. Pat. No. 4,883,467.

SUMMARY OF THE INVENTION

An object of the present invention is to provide a valve of the type initially described that is simple in structure and has an extremely high sealing power over a comparatively long time period.

This object is achieved in accordance with the principles of the present invention in a liquid which is insoluble in the fluid which flows through the valve and which is contained between the valve part and the valve seat so as to serve as a seal, or at least a portion of a seal. When a valve having such a seal closes, a deformation of the liquid occurs, whereby an extremely good seal is obtained. The deformation power of the seal is of approximately the same size or less than that of a seal manufactured of an elastic material. When the valve is opened, the seal reassumes its original shape and is thus free of aging phenomena to which a conventional seal is usually exposed, since the conventional seal is given a permanent deformation over time which could jeopardize the sealing function of the valve, as set forth above.

In a further embodiment of the invention the sealing liquid forms a drop that is partly surrounded by a cavity provided in the valve. Such a seal is suitable for a valve that is intended to seal the discharge of a gas or liquid chamber in, for example, a medication dosing device whose discharge opening has an extremely small diameter.

In another embodiment of the invention the valve seat or the valve part is provided with an annular cavity that at least partly surrounds the sealing liquid. Such a liquid seal is suitable for a valve having a discharge opening for gas or liquid that has a diameter that is larger in comparison to the aforementioned discharge opening.

According to the invention, the sealing liquid has a surface tension and shape such that the internal pressure generated as a result thereof is greater than the pressure of that gas or that liquid that the valve is intended to seal. Due to the surface tension T of the liquid, an excess pressure P arises in this drop-shaped liquid seal. The following relationship thereby exists:

$P=2\ T/r$, whereby r is the radius of the drop.

Given realistic values in this equation and with a diameter of the discharge of the gas or liquid chamber that amounts to a few tenths of a millimeter, the surface tension can hold the drop together up to a pressure that is adequate for many applications.

Since the surface tension, among other things, arises in the boundary surface between two liquids, the sealing liquid must be selected in view of the liquid that is to be pumped. In an insulin pump, the sealing liquid is preferably a polymeric liquid.

In conjunction with further applications, the sealing liquid is preferably composed of mercury.

Thus, as used herein "containing" the seal liquid means preventing uncontrolled flow or spreading of the seal liquid, and this can be accomplished by physically, mechanically confining the seal liquid, or by carrying the seal liquid so that its shape and surface tension provide the containment, or by a combination of these techniques.

In a version of the valve of the type initially described wherein the valve part is formed of a magnetizable material that is influenced by at least one magnet preferably arranged at the valve seat, in accordance with the invention the sealing liquid is composed of a magnetic liquid. A reliable seal with the aforementioned advantages is obtained by placing a magnetic liquid on the valve seat and/or on the valve part, even when the valve seat and/or the valve part exhibit small imperfections.

In a version of this embodiment According of the invention, a part of the valve that comprises no magnetic liquid is provided with a conventional seal. In this version, too, an extremely good seal having a long service life is obtained.

According to the invention, the magnetic liquid is composed of a suspension of extremely small particles of magnetic material in a liquid. The magnetic material of the liquid is pulverized and treated such that the chemical properties thereof are normally hidden (masked by) in the liquid in which the material is suspended.

DESCRIPTION OF THE DRAWINGS

FIGS. 2–6 show further enlarged views of the discharge system of the medication pump of FIG. 1 respectively having valves in various positions and in various embodiments of the invention.

DESCRIPTION OF THE PREFERRED EMBODIMENTS

Figure 1:
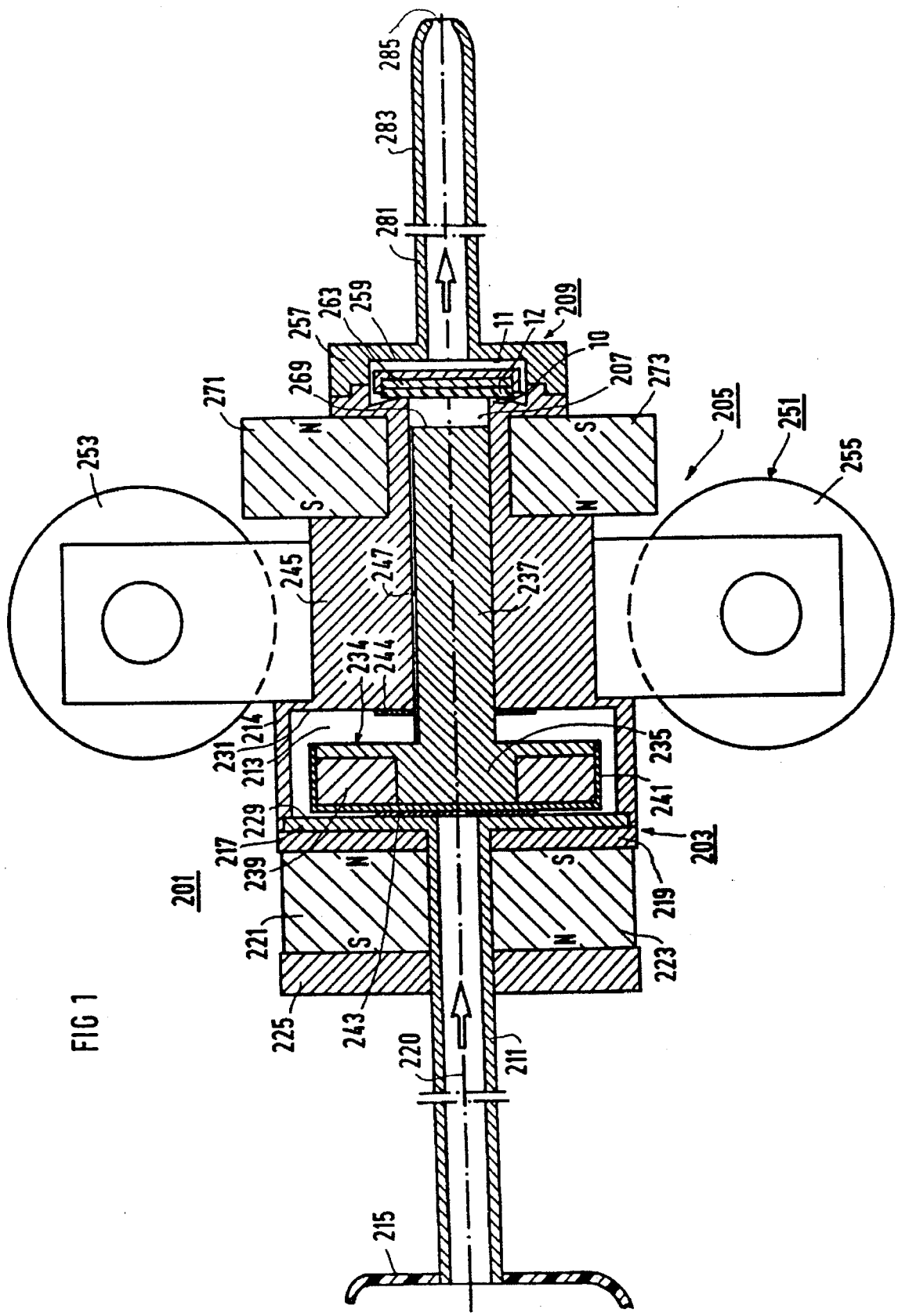
FIG. 1 is an enlargement of a longitudinal section through medication pump having a valve constructed in accordance with the principles of the present invention.

FIG. 1 shows an enlarged view of an implantable medication pump 201 for a medication conveying volume of approximately 1 μl.

This medication pump 201, which is of the piston pump type, is essentially composed of an admission system 203 having a magnetic restoring spring, a pump system 205 having a pump chamber 207, and of a discharge system 209 having an integrated one-way valve.

The admission system 203 has a fluid tract that has an intake line 211 and a cylindrical admission chamber 213 in a housing 214. A medication reservoir 215 that is preferably charged with under-pressure compared to its environment, for example at 300 mbar, is connectable to the intake line 211. In particular, the reservoir 215 can be a container with insulin. The intake line 211 discharges via a flange 217 into the admission chamber 213.

A non-magnetizable, cylindrical carrying member 219 is seated on the end piece of the intake line 211, two permanent magnets 221 and 223 being arranged at the carrier member 219 diametrically relative to the axis 220. These magnets 221 and 223, for example, are each of a cylindrical or cuboid shape and have the shown oppositely oriented polarities S-N and N-S.

An axially displaceable cylindrical armature 234 is located in the admission chamber 213. This armature 234 has an armature carrier 235 whose right end merges into a longer piston 237 having a smaller diameter.

In the illustrated exemplary embodiment, an annular armature part 239 is secured on the armature carrier 235. The armature part 239 is inverted over the core of the armature carrier 235 that merges into the piston 237. The armature part 239 is fabricated of a magnetizable material, for example soft iron. The armature carrier 235 is partially surrounded or framed, and the armature part 239 is completely surrounded or framed, by a cylindrical socket or capsule 241.

The permanent magnets 221 and 223 placed outside the admission chamber 213 constantly exert a force on the armature 234 that attracts the armature 234 together with the piston 237 in the direction toward the intake line 211 but which does not close the admission opening in the flange 217. A detent 243, for example in the form of a thin, annular and centrally secured plate, can be provided at the end face 229 of the flange 217 for limiting this retraction motion. A further detent 244, likewise having the form of a thin, axially placed ring, can be attached to the other end face 231 of the admission chamber 213. When the armature 234 is located at the left end face 229, the piston 237 is in its dead position or quiescent position.

The two permanent magnets 221 and 223 plus the carrier member 219 and the return part 225 are preferably displaceable in defined fashion in the direction of the longitudinal axis 220, as a result of which the restoring force on the armature 234, and thus on the piston 237, can be continuously set to a desired value The piston 237 is longitudinally displaceable in a cylinder 245. A gap 247, particularly an annular gap, is provided between cylinder 245 and piston 237, the liquid medication being conveyed from left to right through this annular gap when the piston 237 returns into its quiescent position, as described in greater detail below.

The armature 234, in combination with a ferromagnetic armature part 239, simultaneously serves as armature for an electromagnetic drive system 251 that is arranged at the cylinder 245. This system has two electromagnetic coils 253 and 255. When these coils 253 and 255 are excited with a current, a magnetic field is generated that exerts a sufficiently large influencing force on the armature 234. As a result, the armature 234 together with the piston 237 is displaced in the direction toward the discharge system 209, until the armature 237 strikes the right end face 231 or against the detent 244.

A valve 13 having a valve seat 10, a valve part 11 displaceable relative to the valves seat 10, and a seal 12 therebetween is located downstream directly behind the pump chamber 207. The valve 13 is accommodated in a carrier flange 257 that forms a discharge chamber 259.

The valve part 11 is fabricated with an element 263 of magnetizable material and serves as an armature. Together with two permanent magnets 271 and 273 that are attached in the cylinder 245 around the center axis 220 with the indicated oppositely oriented polarities S-N and N-S, the element 263 forms a magnetic spring system. The magnetic spring system formed by the magnets 271 and 273 and the element 263 holds the valve part 11 in a quiescent position wherein the valve part 11 presses the seal 12 against the valve seat 10. The valve 13 with the seal 12 of the invention is described in greater detail below in combination with FIGS. 2–6.

A discharge line 281 that merges into a catheter 283 having a discharge opening 285 adjoins the discharge chamber 259 with the valve part 11 via the attachment flange 257. In the implantation, the discharge opening 285 is positioned at a predetermined site in the patient.

During operation of the piston pump 201, the piston 237 is moved out of the illustrated quiescent position toward the right by the electromagnetic field effect of the coils 253 and 255, as a result of which a pronounced over-pressure arises in the medication in the pump chamber 207. As soon as the force exerted on the movable valve part 11 by the over-pressure exceeds the restoring force of the magnetic spring 263, 271, 273, the valve part 11 together with its seal 12 lifts off from the valve seat 10. A valve gap is formed between the valve part 11 and the valve seat 12. The liquid medication, for example, insulin, is expressed via the discharge line 281 into the catheter 283. The catheter 283 is thereby directly connected to the discharge chamber 259. The liquid medication contained in the pump chamber 207 thereby flows through the valve gap, the discharge chamber 259 and the catheter 283 in the direction of the arrow.

After the coils 253 and 255 are de-energized, the piston 237 returns to its dead position shown in FIG. 1, causing an under-pressure to be generated in the pump chamber 207. When the absolute value thereof is lower than that in the medication reservoir 215, a pressure gradient arises. The liquid medication is thereby suctioned into the pump chamber 207 against the under-pressure in the medication reservoir 215 by the greater under-pressure in the pump chamber 207. The liquid flows through the gap 247 between the piston 237 and the cylinder 245. The valve part 11 and the valve seat 10 thereby act as a one-way valve. After the de-energization of the coils 253 and 255, the armature 234 together with piston 237 is returned to its dead position or quiescent position by the permanent magnets 221 and 223 that act on the armature part 239. When insulin is to be administered again to the patient, the described pump process is repeated.

Figure 2:
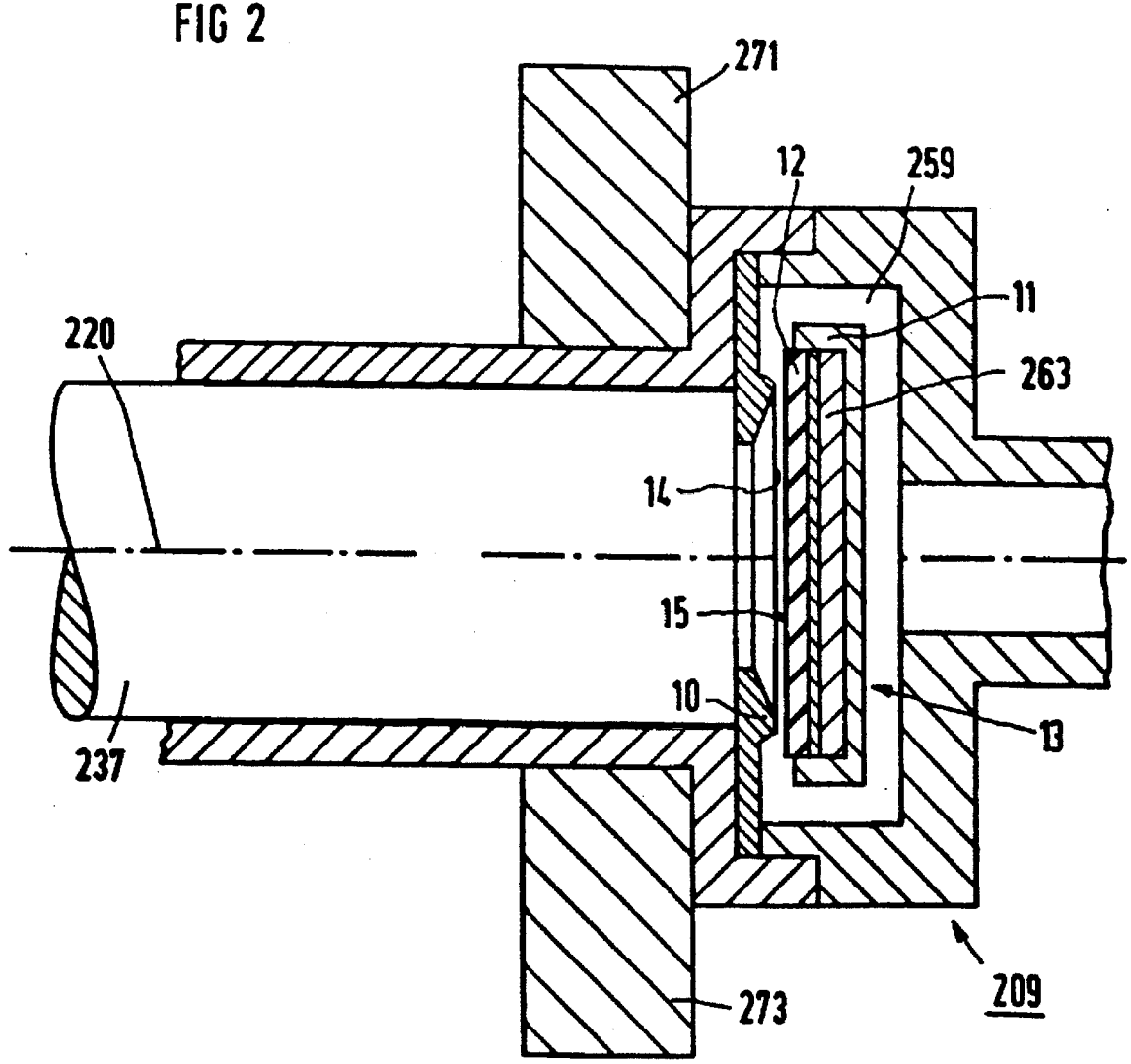

The valve 13 is clearly illustrated in FIG. 2, which is a further enlargement of the discharge system 209 of the medication pump 201 shown in FIG. 1. By contrast to the valve 13 in FIG. 1, the valve 13 in FIG. 2 is shown in the open position described above in conjunction with FIG. 1. In this open position, the valve part 11 is situated in a position wherein the seal 12 thereof does not press tightly against the valve seat but has the spacing of a gap aperture relative to the valve seat, so that the flowing medication can flow through the valve gap into the discharge chamber 259. The medication is subsequently conveyed via the discharge line 281 into the catheter 283 shown and described in conjunction with FIG. 1.

The valve seat 10 of the valve 13 is provided with a layer or film of magnetic liquid referenced 14 in FIG. 2. The magnetic liquid adheres to the valve seat 10 since two permanent magnets 271 and 273-as set forth-are arranged at the valve seat 10. Since the valve part 11 contains an element 263 composed of a magnetizable material, it is also possible to coat the seal 12 of the valve part 11 with a magnetic liquid referenced 15.

If only one of the layers or films 14 or 15 is applied onto one of said parts 10 or 11, the part of the valve 13 that is not coated with a magnetic liquid is provided with a conventional seal. The magnetic liquid of the layer 14 or 15 is composed of a suspension of extremely small particles of a magnetic material in a viscous, organic liquid. The magnetic liquid of the layer 14 or 15 exhibits such properties such that it is insoluble in the liquid that flows through the valve. The magnetic liquid is also inert with respect to the liquid with which it comes into contact. By coating the valve seat 10 and/or the seal 12 of the valve part 11 with a magnetic liquid, an extremely good seal is obtained when the valve 13 closes even when the valve seat 10 and/or the seal exhibits irregularities or when the seal 12—which is usually a membrane—exhibits aging phenomena. When the valve part 11 presses against the valve seat 10, the layer or layers 14 or 15 of the magnetic liquid are deformed. An extremely good seal is obtained in this way.

Figure 3:
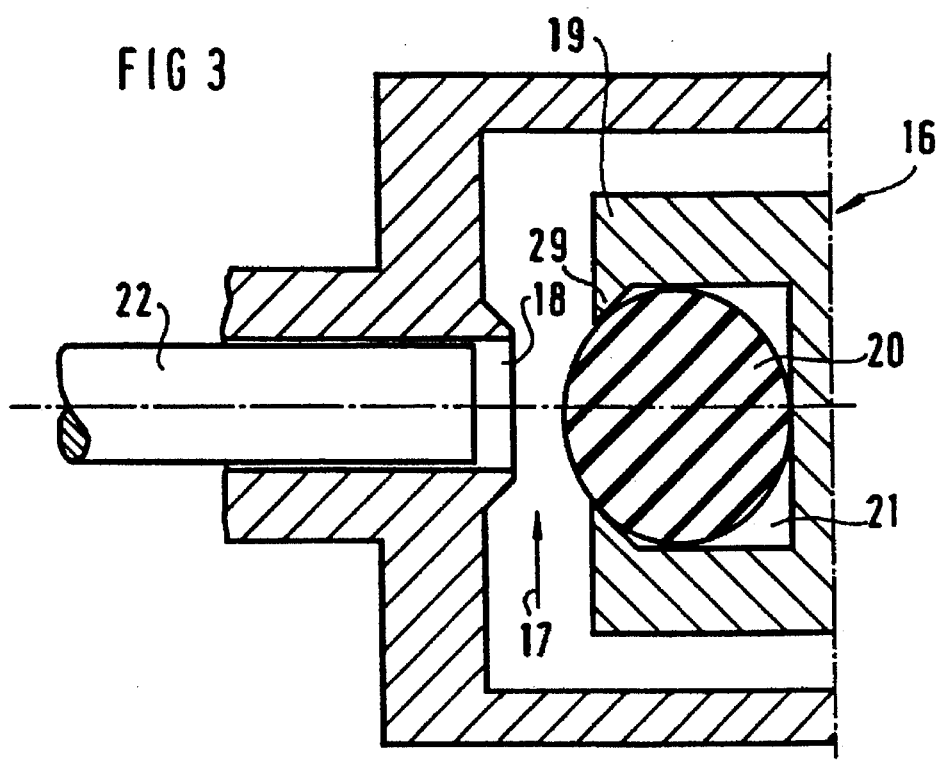
Figure 4:
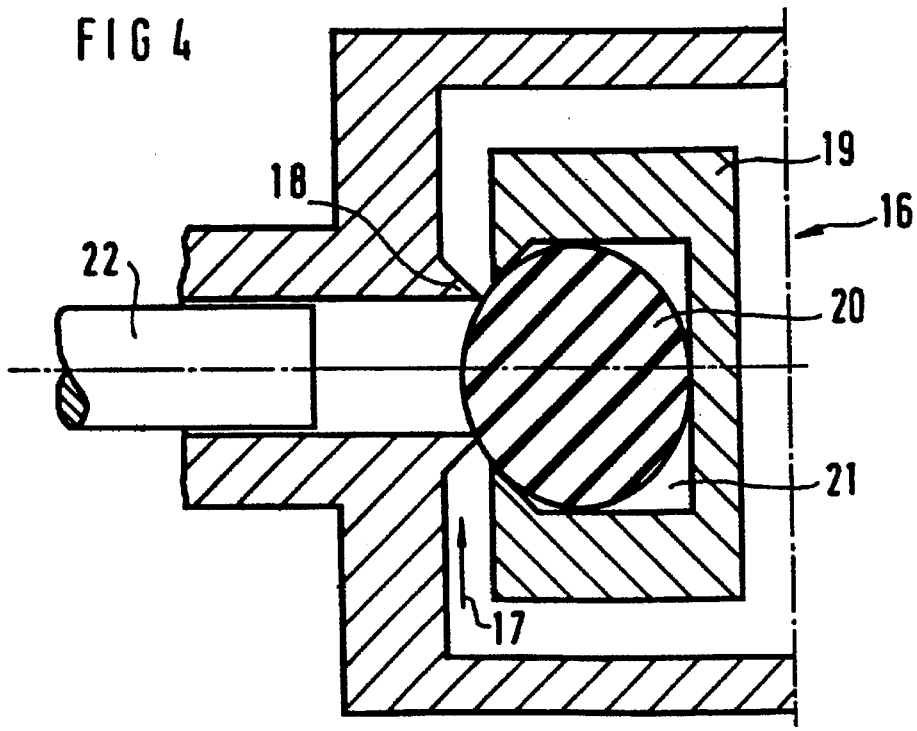

FIG. 3 shows an enlargement of a discharge system 16 having a valve 17; the discharge system can be part of a medication pump of FIG. 1. The discharge system, however, can also be a part of a device for dosing gasses or liquids wherein the pump is not necessarily driven with a magnetic spring system. The valve 17 also has a valve seat 18, a valve part 19 displaceable relative to the valve seat 18 and a seal 20. The seal 20 is composed of a liquid that forms a drop that is partly surrounded by a cavity 21 provided in the valve part 19. Since the cavity 21 is somewhat smaller than the size of the drop and is provided with an annular lip 29, the drop is automatically held at its location. Similar to the aforementioned magnetic liquid, this sealing liquid has properties such that it is insoluble in the liquid or in the gas that flows through the valve. The drop-shaped sealing liquid 20 has a surface tension such that the internal pressure produced as a result thereof is higher than the pressure of that of the gas or liquid that the valve is intended to seal. In this FIG. 3, the valve is shown in an open position wherein a pump piston 22 has influenced a medium to press against the drop-shaped sealing liquid 20 such that the sealing liquid together with the valve part 19 lift off from the valve seat 18, so that a gap opening for the medium is formed. When the piston is subsequently displaced in the opposite direction, an underpressure is formed in front of the piston, whereby the valve part 19 and, most importantly, the drop-shaped sealing liquid 20 is pressed against the valve seat 18, so that the liquid 20 is subsequently deformed, as shown in FIG. 4. An extreme seal is obtained as a result thereof. When the valve 17 is opened again, the sealing liquid 20 reassumes its original drop shape. The sealing liquid 20 is preferably a polymer. The sealing liquid can alternatively be composed of mercury.

FIGS. 5 and 6 show an enlargement of a further discharge system 23 having a valve 24. The discharge system 23 can be a part of a device for dosing gasses or liquids. The valve 24 has a valve seat 25, a valve part 26 displaceable relative to the valve seat 25, and a seal 27. The valve part 26 is provided with an annular cavity 28 that partly surrounds the seal 27. This seal 27, which preferably is oval-shaped in profile, is also composed of a liquid, for example mercury or a polymer. In FIG. 5, the valve 24 is shown in an open position and the valve 24 is shown in a closed position in FIG. 6. In the closed position, the oval-shaped liquid is deformed and thereby seals extremely well against the valve seat 25. The annular cavity 28 having the sealing liquid 27 can also be arranged in the valve seat 25 according to the invention, as shown in FIG. 5a. In such an exemplary embodiment, the valve part 26 can be provided with a conventional seal. Such a liquid seal according to FIGS. 5 and 6 is suitable for a valve that is intended to seal a discharge for a gas or liquid chamber having a comparatively large diameter.

It is important that the valves which control the flow in a pump operate with a minimal consumption of energy both when opening and when closing the valves. This is of great significance, particularly when a high precision is required in the dosing and/or when small conveying volumes are to be pumped. As a result of the invention disclosed herein, a seal can be deformed with the lowest possible force, so that it seals extremely well and thereby prevents leakage in the region of the range of expected (normal) operating pressure.

Although modifications and changes may be suggested by those skilled in the art, it is the intention of the inventor to embody within the patent warranted hereon all changes and modifications as reasonably and properly come within the scope of his contribution to the art.

I claim as my invention:

1. A valve for controlling a fluid flow comprising:

an inlet for a fluid flow, said fluid flow having a fluid flow pressure;

an outlet for said fluid flow;

a housing disposed between said inlet and said outlet;

a valve seat disposed in said housing between said inlet and outlet and a valve part movably disposed in said housing to press against said valve seat to block fluid flow and to move away from said valve seat to permit fluid flow;

a liquid which is insoluble in said fluid flow, said liquid having a surface tension; and means for containing said liquid for causing said liquid to interact between said valve part and said valve seat when said valve part is against said valve seat for forming a seal, by giving said liquid a shape which, in combination with said surface tension, produces an internal pressure of said seal which is higher than said pressure of said fluid flow.

2. A valve as claimed in claim 1 wherein said means for containing said liquid comprises a cavity partially surrounding said liquid and forming said liquid into a drop in said cavity.

3. A valve as claimed in claim 1 wherein said valve seat comprises an annular cavity, said annular cavity forming a part of said means for containing said liquid.

4. A valve as claimed in claim 1 wherein said liquid comprises mercury.

5. A valve as claimed in claim 1 wherein said liquid comprises a polymeric liquid.

6. A valve as claimed in claim 1 wherein said valve part and said valve seat comprise valve elements, and wherein one of said valve elements consists of magnetic material and the other of said valve elements consists of non-magnetic material, wherein said valve further comprises a magnet which generates a magnetic field in which said valve elements are disposed, and further comprising a mechanical, non-liquid seal carried by said one said valve elements comprised of non-magnetic material.

7. A valve as claimed in claim 1 wherein said liquid comprises liquid which is chemically inert with respect to said fluid flow.

8. A valve as claimed in claim 1 for use with a reservoir of insulin and an insulin pump, said valve being disposed in said insulin pump for controlling a flow of insulin from said reservoir through said insulin pump as said fluid flow.

9. A valve for controlling a fluid flow comprising:

an inlet for a fluid flow;

an outlet for said fluid flow;

a housing disposed between said inlet and said outlet;

a valve seat disposed in said housing between said inlet and outlet and a valve part comprised of a magnetizable material movably disposed in said housing to press against said valve seat to block fluid flow and to move away from said valve seat to permit fluid flow;

a magnetizable liquid which is insoluble in said fluid flow; and means for containing said magnetizable liquid for causing said magnetizable liquid to interact between said valve part and said valve seat when said valve part is against said valve seat for forming a seal, said means for containing said magnetic liquid including said valve part and a magnet which generates a magnetic field in which said valve part and said liquid are disposed.

10. A valve for controlling a fluid flow comprising:

an inlet for a fluid flow;

an outlet for said fluid flow;

a housing disposed between said inlet and said outlet;

a valve seat disposed in said housing between said inlet and outlet and a valve part comprised of a magnetizable material movably disposed in said housing to press against said valve seat to block fluid flow and to move away from said valve seat to permit fluid flow;

a magnetizable liquid which is insoluble in said fluid flow; and means for containing said magnetizable liquid for causing said magnetizable liquid to interact between said valve part and said valve seat when said valve part is against said valve seat for forming a seal, said means for containing said magnetizable liquid including said valve seat, said valve part and a magnet which generates a magnetic field in which said valve part, said valve seat and said magnetic liquid are disposed.

11. A valve for controlling a fluid flow comprising:

an inlet for a fluid flow;

an outlet for said fluid flow;

a housing disposed between said inlet and said outlet;

a valve seat disposed in said housing between said inlet and outlet and a valve part comprised of magnetizable material movably disposed in said housing to press against said valve seat to block fluid flow and to move away from said valve seat to permit fluid flow;

a magnetizable liquid which is insoluble in said fluid flow, said magnetizable liquid comprising a suspension of particles of magnetic material in a liquid; and means for containing said magnetizable liquid for causing said magnetizable liquid to interact between said valve part and said valve seat when said valve part is against said valve seat for forming a seal, said means for containing said magnetizable liquid including said valve part and a magnet which generates a magnetic field in which said valve part and said magnetizable liquid are disposed.

12. A valve as claimed in claim 11 wherein said liquid in which said particles of magnetic material are suspended comprises a viscous organic liquid.

13. A valve for controlling a fluid flow comprising:

an inlet for a fluid flow;

an outlet for said fluid flow;

a housing disposed between said inlet and said outlet;

a valve seat disposed in said housing between said inlet and outlet and a valve part movably disposed in said housing to press against said valve seat to block fluid flow and to move away from said valve seat to permit fluid flow, said valve part and said valve seat comprising valve elements, with one of said valve elements consisting of magnetic material and the other of said valve elements consisting of non-magnetic material;

a liquid which is insoluble in said fluid flow;

means for containing said liquid for causing said liquid to interact between said valve part and said valve seat when said valve part is against said valve seat for forming a seal;

a magnet which generates a magnetic field in which said valve elements are disposed for interacting with said one of said valve elements consisting of magnetic material; and a mechanical, non-liquid seal carried by the other of said valve elements comprised of non-magnetic material.

* * * * *